(12) United States Patent
Amir

(10) Patent No.: US 9,841,370 B2
(45) Date of Patent: Dec. 12, 2017

(54) MULTI-LAYERED TARGET DESIGN

(71) Applicant: KLA-TENCOR CORPORATION, Milpitas, CA (US)

(72) Inventor: Nuriel Amir, St. Yokne'am (IL)

(73) Assignee: KLA-Tencor Corporation, Milpitas, CA (US)

( * ) Notice: Subject to any disclaimer, the term of this patent is extended or adjusted under 35 U.S.C. 154(b) by 263 days.

(21) Appl. No.: 14/620,992

(22) Filed: Feb. 12, 2015

(65) Prior Publication Data
US 2015/0153268 A1 Jun. 4, 2015

Related U.S. Application Data

(63) Continuation of application No. PCT/US2014/039833, filed on May 28, 2014.

(60) Provisional application No. 61/828,578, filed on May 29, 2013.

(51) Int. Cl.
| | | |
|---|---|---|
| *G01J 1/10* | (2006.01) | |
| *G01N 21/01* | (2006.01) | |
| *G03F 7/20* | (2006.01) | |
| *G01N 21/95* | (2006.01) | |
| *G06F 17/50* | (2006.01) | |

(52) U.S. Cl.
CPC ......... *G01N 21/01* (2013.01); *G01N 21/9501* (2013.01); *G03F 7/70616* (2013.01); *G06F 17/5072* (2013.01); *G06F 17/5081* (2013.01); *G01N 2201/02* (2013.01); *G01N 2201/12* (2013.01); *Y10T 428/2457* (2015.01)

(58) Field of Classification Search
CPC .. G01N 21/93; G01N 21/278; G01N 21/4785; G01N 21/64; H01L 22/34
USPC ...................................................... 356/243.4
See application file for complete search history.

(56) References Cited

U.S. PATENT DOCUMENTS

| | | | |
|---|---|---|---|
| 7,242,477 B2 * | 7/2007 | Mieher | G01N 21/956 356/401 |
| 7,608,468 B1 * | 10/2009 | Ghinovker | G03F 7/70633 356/401 |
| 8,243,273 B2 | 8/2012 | Levinski et al. | |
| 9,255,892 B2 * | 2/2016 | Van De Kerkhof | G03F 7/70633 |
| 2003/0223630 A1 | 12/2003 | Adel et al. | |
| 2004/0257571 A1 * | 12/2004 | Mieher | G01N 21/956 356/401 |
| 2005/0105092 A1 | 5/2005 | Ausschnitt et al. | |
| 2005/0193362 A1 | 9/2005 | Phan et al. | |
| 2008/0121939 A1 * | 5/2008 | Murray | G03F 1/36 257/202 |
| 2011/0069314 A1 | 3/2011 | Ausschnitt et al. | |
| 2011/0248388 A1 | 10/2011 | Ausschnitt et al. | |
| 2012/0033215 A1 | 2/2012 | Kandel et al. | |
| 2013/0107259 A1 | 5/2013 | Choi et al. | |

* cited by examiner

*Primary Examiner* — Tarifur Chowdhury
*Assistant Examiner* — MD M Rahman
(74) *Attorney, Agent, or Firm* — Suiter Swantz pc llo

(57) ABSTRACT

Multi-layered targets, design files and design and production methods thereof are provided. The multi-layered targets comprise process layers arranged to have parallel segmentation features at specified regions, and target layer comprising target elements which are perpendicular to the parallel segmentation features of the process layers at the specified regions.

39 Claims, 9 Drawing Sheets

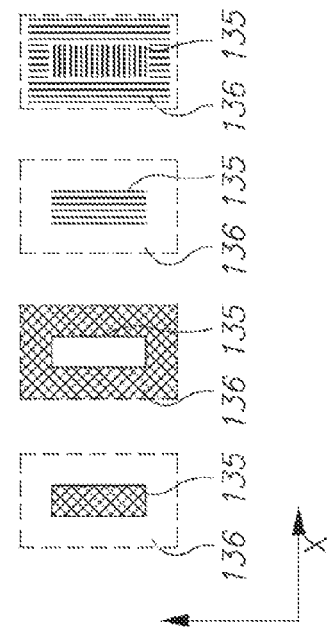
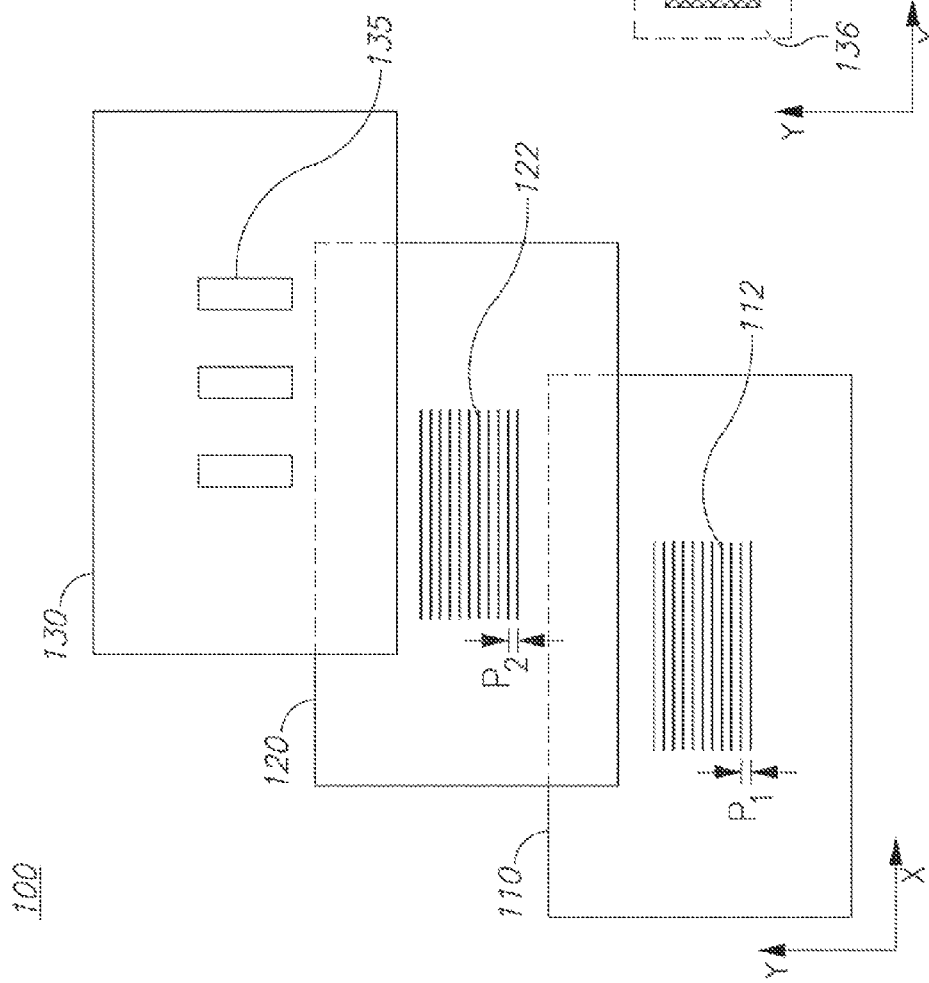
Figure 1A
Figure 1B

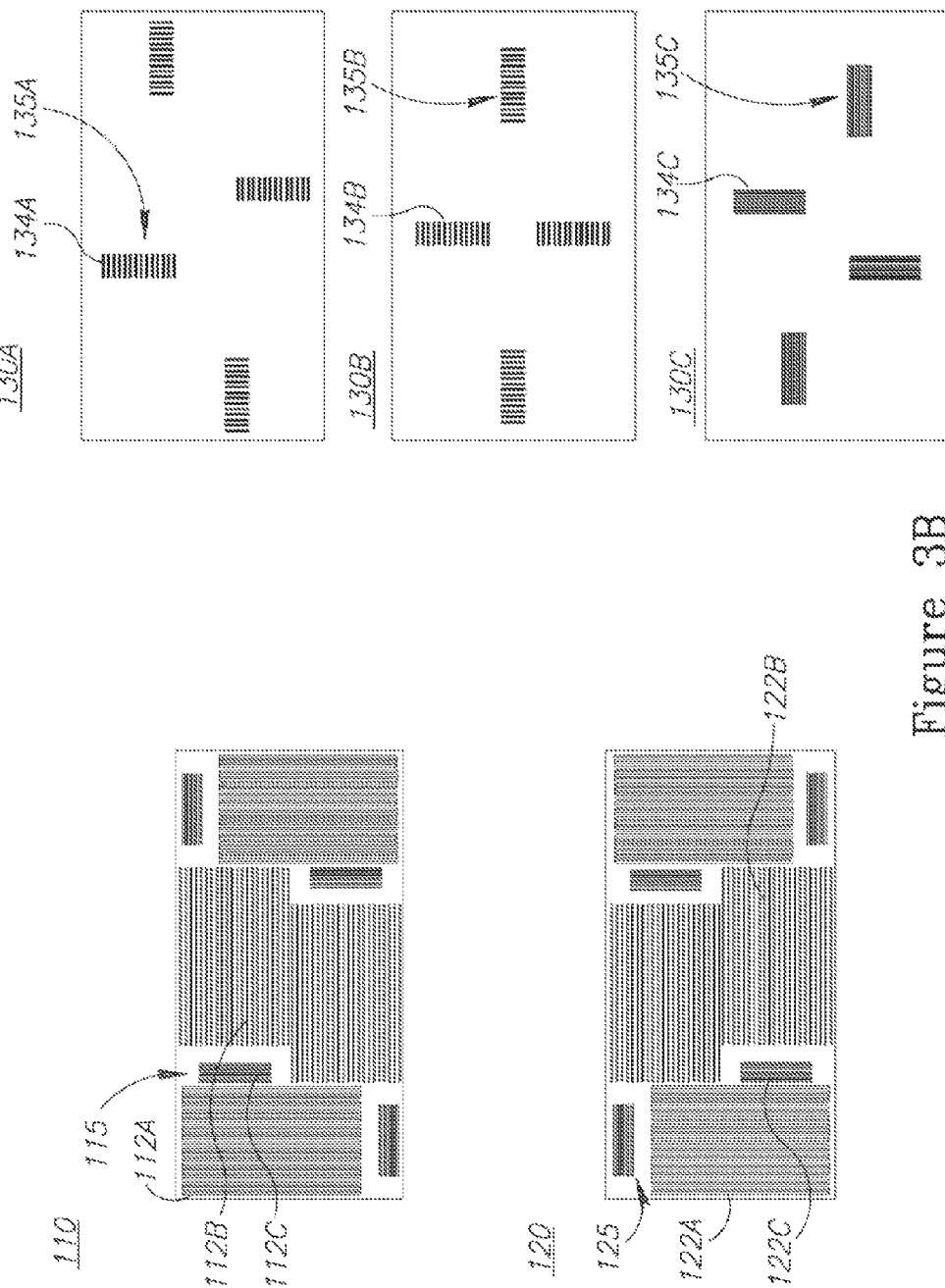

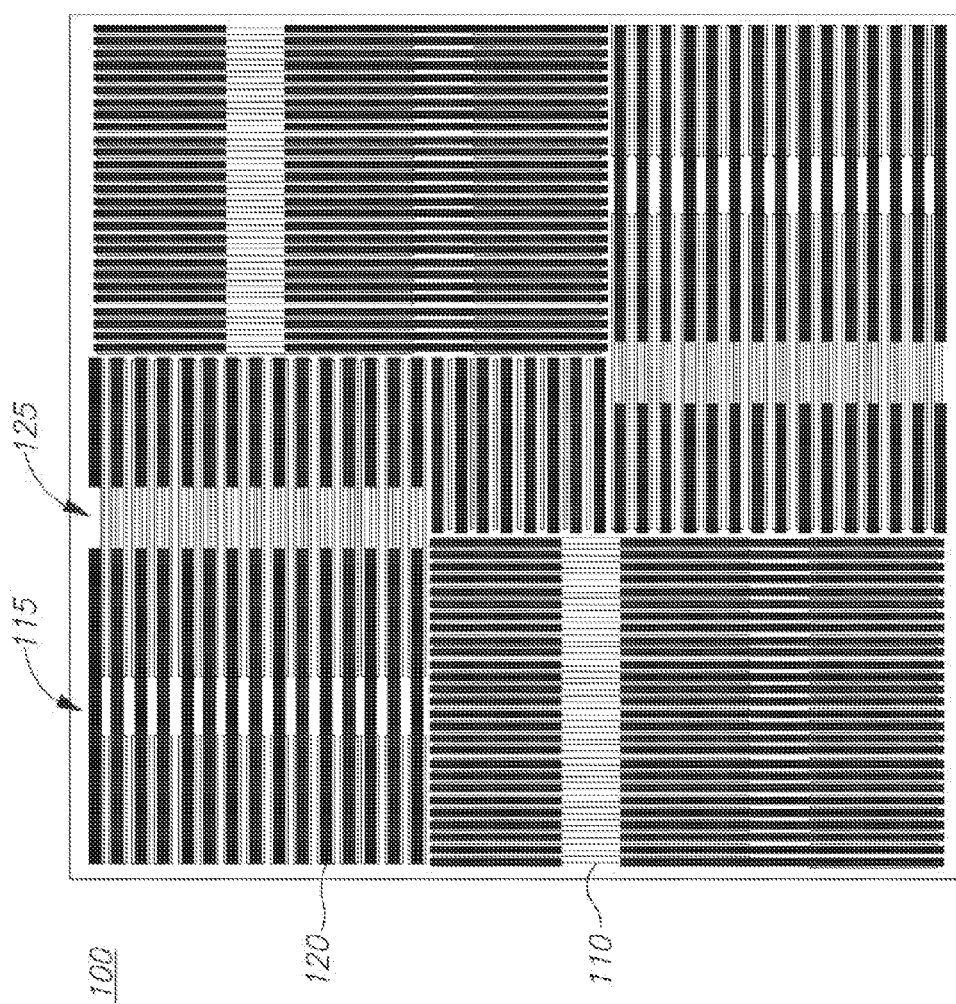

*200*

- 210 — DESIGNING AT LEAST TWO PROCESS LAYERS OF A MULTI-LAYERED TARGET TO HAVE PARALLEL SEGMENTATION FEATURES AT SPECIFIED REGIONS
- 215 — PRODUCING THE PROCESS LAYERS TO HAVE PARALLEL SEGMENTATION FEATURES AT SPECIFIED REGIONS
- 220 — CONFIGURING TARGET ELEMENTS OF AT LEAST ONE TARGET LAYER OF THE MULTI-LAYERED TARGET TO BE PERPENDICULAR TO THE PARALLEL SEGMENTATION FEATURES OF THE PROCESS LAYERS AT THE SPECIFIED REGIONS
- 225 — PRODUCING THE TARGET ELEMENTS TO BE PERPENDICULAR TO THE PARALLEL FEATURES OF THE OTHER LAYERS AT THE SPECIFIED REGIONS
- 230 — CONFIGURING THE PARALLEL SEGMENTATION FEATURES OF THE PROCESS LAYERS TO HAVE THE SAME SEGMENTATION PITCH OR AT LEAST NOT TO FORM MOIRÉ PATTERN(S)
- 240 — DESIGNING THE PARALLEL FEATURES AT SOME OF THE SPECIFIED REGIONS TO BE PERPENDICULAR TO THE PARALLEL FEATURES AT OTHER SPECIFIED REGIONS

Figure 5

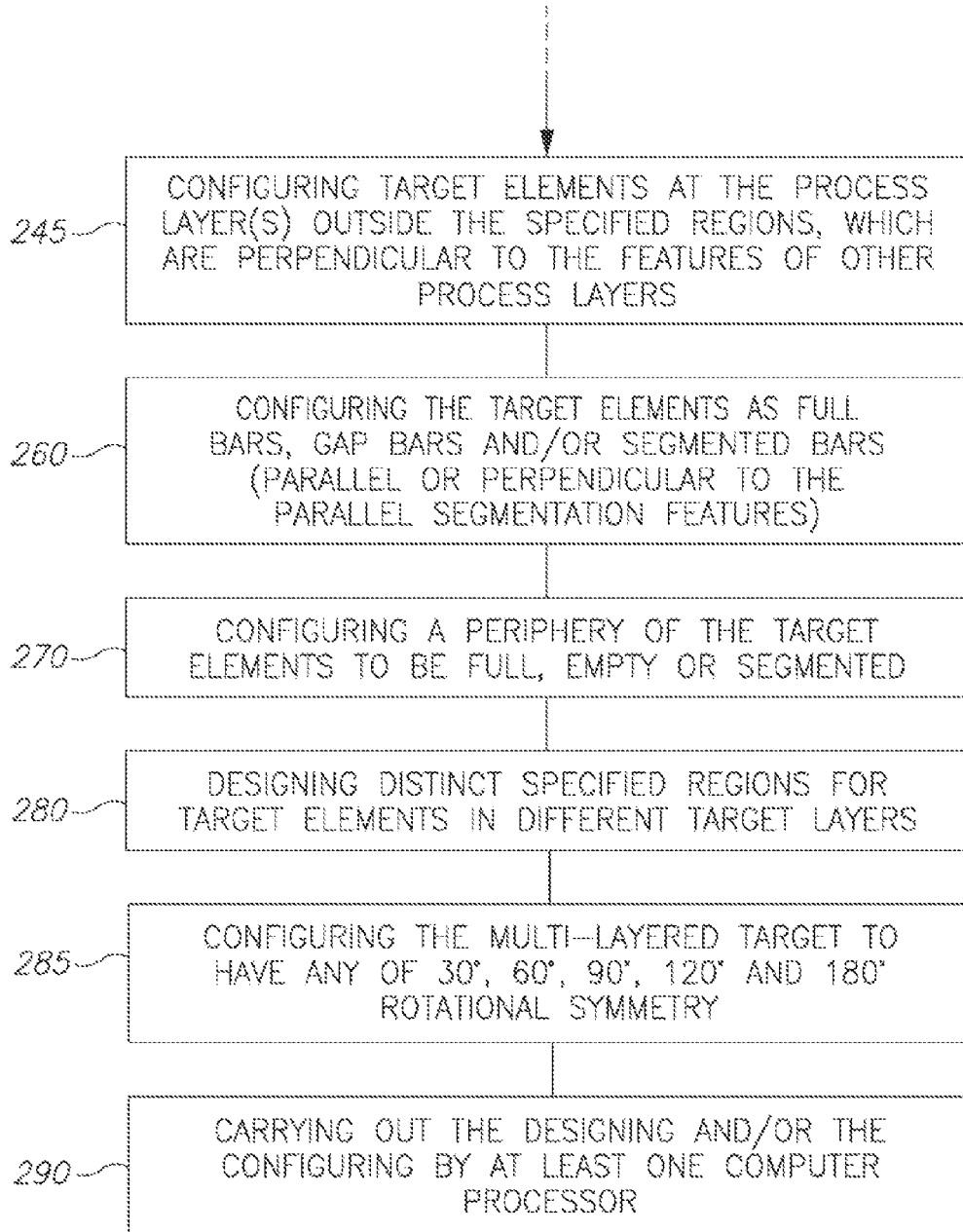
Figure 5 (cont. 1)

MULTI-LAYERED TARGET DESIGN

CROSS-REFERENCE TO RELATED APPLICATIONS

This application is a Continuation of International Patent Application Serial No. PCT/US2014/39833, filed on May 28, 2014, which application claims priority of U.S. Provisional Patent Application No. 61/828,578, filed on May 29, 2013, which applications are incorporated herein by reference.

FIELD OF THE INVENTION

The present invention relates to the field of metrology, and more particularly, to metrology targets.

BACKGROUND OF THE INVENTION

Metrology targets are designed to enable the measurement of parameters that indicate the quality of wafer production steps and quantify the correspondence between design and implementation of structures on the wafer. Metrology targets as specific structures optimize the requirements for device similarity and for optical measurability. Compliance of targets to semiconductor manufacturing design rules contributes to accurate production of the targets but may reduce the optical measurability of the targets.

U.S. Patent Application Publication No. 2012/0033215 and U.S. Pat. No. 8,243,273, which are incorporated herein by reference in their entirety, disclose adding dummyfill to a target design to improve compliance with design rules.

BRIEF SUMMARY OF THE INVENTION

One aspect of the present invention provides a multi-layered target comprising at least two process layers arranged to have parallel segmentation features at specified regions, and at least one target layer comprising target elements which are perpendicular to the parallel segmentation features of the process layers at the specified regions.

These, additional, and/or other aspects and/or advantages of the present invention are set forth in the detailed description which follows, possibly inferable from the detailed description, and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. In the accompanying drawings:

FIG. 1A is a high level schematic illustration of multi-layered targets, according to some embodiments of the invention;

FIG. 1B is a high level schematic illustration of target elements and their respective peripheries, according to some embodiments of the invention;

FIG. 3B is a high level schematic illustration of the layers of an exemplary multi-layered target, according to some embodiments of the invention;

FIG. 4A is a high level schematic illustration of an exemplary multi-layered target, according to some embodiments of the invention;

DETAILED DESCRIPTION OF THE INVENTION

Figure 2A:
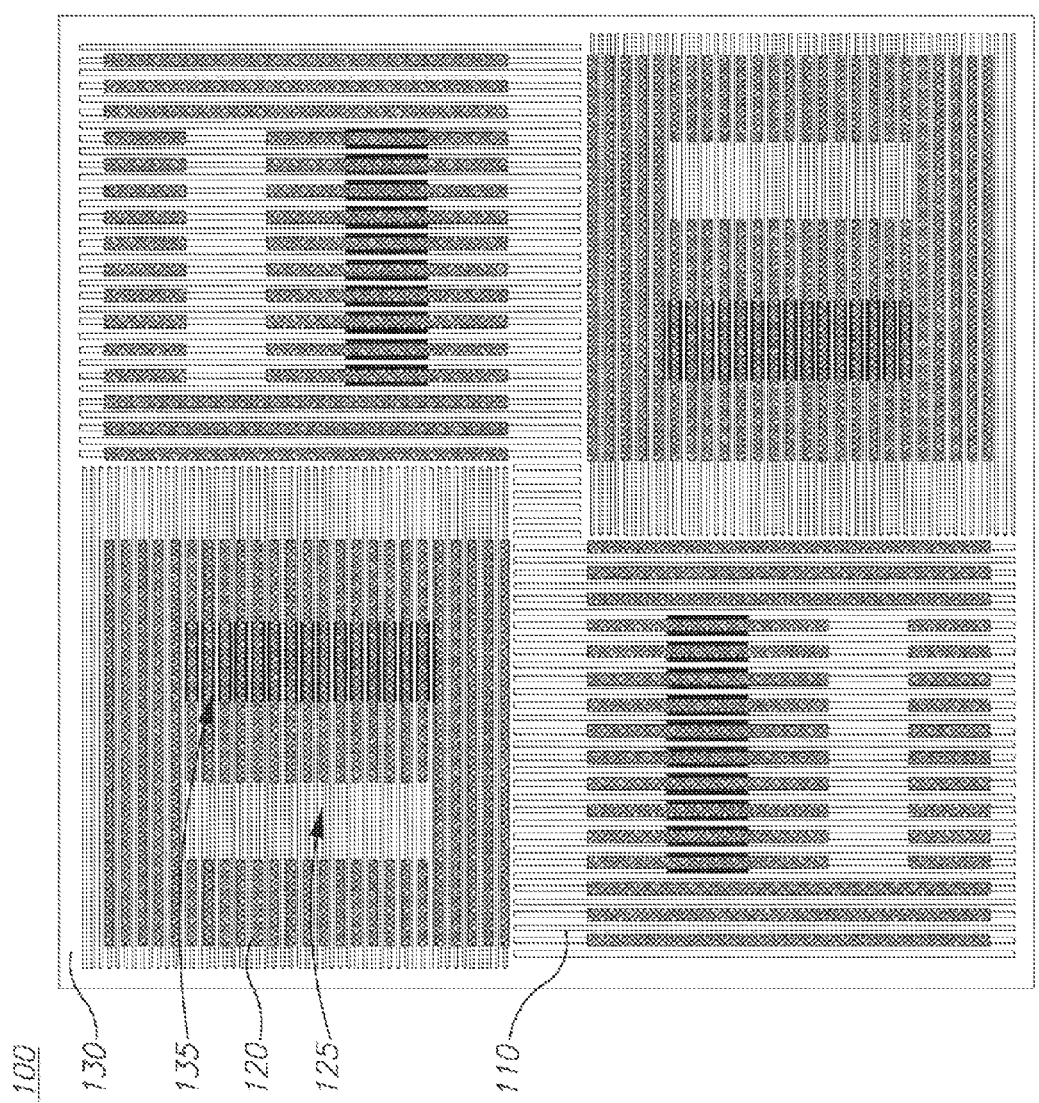
FIG. 2A is a high level schematic illustration of an exemplary multi-layered target, according to some embodiments of the invention.

Prior to the detailed description being set forth, it may be helpful to set forth definitions of certain terms that will be used hereinafter.

The terms "metrology target" or "target" as used herein in this application, are defined as structures designed or produced on a wafer which are used for metrological purposes. The term "target element" as used herein in this application, is defined as a feature in the metrology target such as individual target areas or boxes, grating bars, etc. Target elements may be full or empty (gaps), and may also be segmented, i.e., may comprise multiple smaller features which cumulatively constitute the target element. A target is referred to as comprising target elements, each "target element" being a feature of the target that is to be distinguished from its background, the "background" being a wafer area proximate to a target element on the same or on a different layer (above or below the target element). Specifically, the term "periphery" of a target element refers to the immediate layer around the target element in the same layer. The term "specified region" as used herein in this application, is defined as a region of the target which surrounds a target element, i.e., the specified region includes the target element itself and its immediate background.

The terms "layer," "process layer," and "target layer," as used herein in this application, are defined as any of the layers used in a photolithography process in any of its steps. The term "target layer" is used to distinguish a layer with target elements which are to be measured from other layers, yet "process layers" may also hold target elements which may be measured sequentially of simultaneously with respect to target elements of the target layer. Hence, the notation of layers as process layers and target layers is not to be understood as limiting the invention but as merely helping to clarify the target structure and design principles. Examples for layers, which are used in a non-limiting manner in the present disclosure, include oxide or oxide diffusion (OD) layers, polysilicon (poly) layers and contact layers.

The term "periodic structure" as used in this application refers to any kind of designed or produced structure in at least one layer which exhibits some periodicity. The periodicity is characterized by its pitch, namely its spatial frequency. For example, a bar as a target element may be produced as a group of spaced parallel lines, thereby reducing the minimal feature size of the element and avoiding monotonous regions in the target.

The term "segmentation features" as used in this application refers to any details of an area on a layer which are used to prevent the area from being continuously full or continuously empty (which may be referred to as "dummy-fill"), with respect to the order of magnitude of typical device features. In particular, such details are commonly introduced to enhance the producibility of the target. Often these details, such as the segmentation features, are introduced as parallel lines having pitch values which are process compatible. The term "parallel segmentation features" is defined as any area filling details which are at least to some extent parallel in a certain direction.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1A is a high level schematic illustration of multi-layered targets 100, according to some embodiments of the invention. Multi-layered targets 100 comprise at least two process layers 110, 120 arranged to have parallel segmentation features 112, 122 (respectively) at specified regions, and at least one target layer 130 comprising target elements 135 which are perpendicular to parallel segmentation features 112, 122 of process layers 110, 120 (respectively) at the specified regions. The specified regions themselves are understood as the areas of target elements 135 and their immediate peripheries with respect to layers 110, 120, 130 in multi-layered target 100. The at least one target layer may comprise a plurality of target layers, each having target elements at distinct specified regions. Process layers 110, 120 may also comprise target elements at distinct specified regions. The terms process layer and target layer are used for explanatory reasons and are not to be understood as limiting the possible locations for target elements. Moreover, during the metrology measurements layer may change their roles as process layers and target layers, depending on which target is actually measured.

FIG. 1B is a high level schematic illustration of target elements 135 and their respective peripheries 136, according to some embodiments of the invention. Target elements 135 may be, as exemplified from left to right in FIG. 1B, full bars and/or gap bars (i.e., featureless areas within a periphery with features) and/or bars segmented perpendicularly to the parallel segmentation features of the process layers at the specified regions (e.g., 112 and 122 in 110 and 120, respectively) and/or bars segmented in parallel to the parallel segmentation features of the process layers at the specified regions (e.g., 112 and 122 in 110 and 120, respectively). Periphery 136 of target elements 135 may be exemplified in FIG. 1B in arbitrary and non-limiting relationship to target elements 135, empty, full, or segmented parallel or perpendicular to the parallel segmentation features, as long as optical contrast between target element 135 and its periphery 136 is maintained when using specified measurement configuration (e.g., with or without polarization measurements).

Parallel segmentation features (e.g., 112, 122) of process layers (e.g., 110, 120, respectively) are configured to have pitches (e.g., $p_1$, $p_2$, respectively) which do not form a Moiré pattern between the process layers, as such a pattern may increase measurement inaccuracy or may generate false measurements altogether. Pitches $p_1$ and $p_2$ may be equal, have an integer ratio, or at least have a Moiré pattern pitch which does not disturb the measurements (e.g., $p_1$ and $p_2$ may have a large enough common divider or a ratio of small integers as the pitch ratio).

In certain embodiments, target elements 135 may be bars segmented in parallel to parallel segmentation features 112, 122 of process layers 110, 120 at the specified regions. In such cases, the bar segmentation pitch is selected not to produce a Moiré pattern with the parallel segmentation features (e.g., share a pitch value or have a pitch that forms an integral ratio with the pitch(es) of the parallel segmentation features 112, 122). While the bar itself is perpendicular to the parallel segmentation features 112, 122 and hence produces a measurement along the same direction as the parallel segmentation features 112, 122, it may be segmented at a pitch which creates a Moiré pattern with the parallel segmentation features 112, 122 (in a direction perpendicular to the parallel segmentation features 112, 122, i.e., perpendicular to the direction measurement). While such a Moiré pattern is not useful for the measurement itself, it may be used or configured to facilitate ROI placement or target acquisition.

Figure 2B:
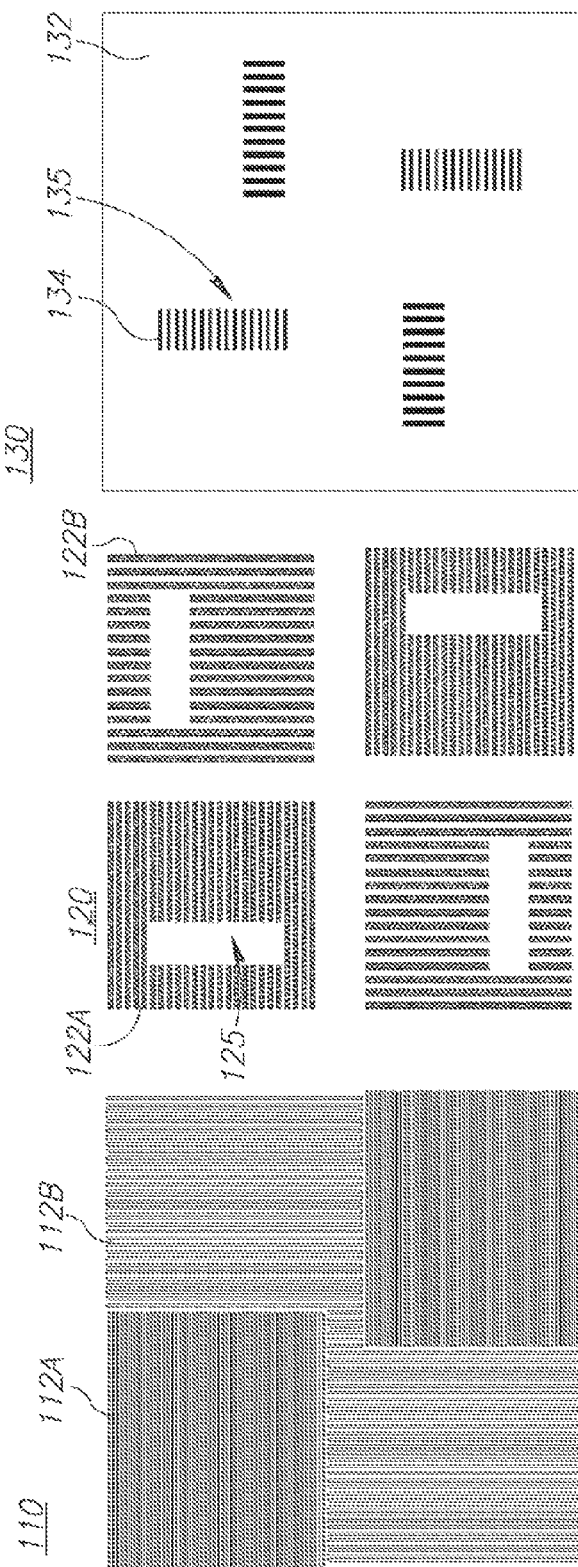
FIG. 2B is a high level schematic illustration of the layers of an exemplary multi-layered target, according to some embodiments of the invention.

FIGS. 2A and 2B are high level schematic illustrations of a multi-layered target 100 and its layers 110, 120, 130, respectively, according to some embodiments of the invention. FIGS. 2A and 2B exemplify in a non-limiting manner process layer 110 (e.g., an oxide diffusion (OD) layer) having segmentation features 112A, 112B which may differ in different regions of layer 110; process layer 120 (e.g., a polysilicon (poly) layer) having segmentation features 122A, 122B which may differ in different regions of layer 120 but are parallel to segmentation features 112A, 112B (respectively) in specified overlapping regions in which segmentation features of layers 110 and 120 are parallel to each other; and target layer 130 (e.g., a contact layer) having target elements 135 in the specified regions in which segmentation features of layers 110 and 120 are parallel to each other. Layers 110, 120, 130 are shown separately in FIG. 2B and overlapping in FIG. 2A. It is noted that target elements 135 are perpendicular to parallel segmentation features of layer 110, 120 in each of the target quartiles.

It is noted that the illustrated identities and order of layers 110, 120 and 130 is non-limiting and any changes thereof are part of the present disclosure. Any of process layers 110, 120 may be below or above target layer 130. Any of layers 110, 120 and 130 may be applied as a positive or a negative layer. For example, target elements 135 may be gaps in a full background 132 of layer 130. In another example, target elements 135 may be segmented, i.e., constructed of segments 134 which cumulatively form target elements 135. In case target element 135 is a gap, segments 134 may be gaps. The pitches of any of the segmentation patterns may vary, particularly of segmentation patterns in different regions of each layer. For example, segmentation pitches in regions 112A and 112B may vary with respect to the direction of segmentation due to production considerations. While pitches may vary, pitches at the specified regions of target elements 135 are designed not to form Moiré patterns, e.g., be identical. In certain embodiments, the parallel segmentation features of the at least two process layers have the same segmentation pitch.

In certain embodiments, at least one of the process layers may comprise, outside the specified regions, target elements which are perpendicular to features of the other process layers. For example, process layer 120 comprises in FIGS. 2A and 2B gap target elements 125 which may be measured with respect to process layer 110. In case background 132 of layer 130 is segmented, its segmentation features in the regions of target elements 125 are parallel to segmentation features 112A, 112B in the respective regions and thus perpendicular to target elements 125. According to such and similar embodiments, process layer 120 and target layer 130 may have alternating roles, depending on the specified regions and target elements 125, 135 in each respective layer.

Figure 3A:
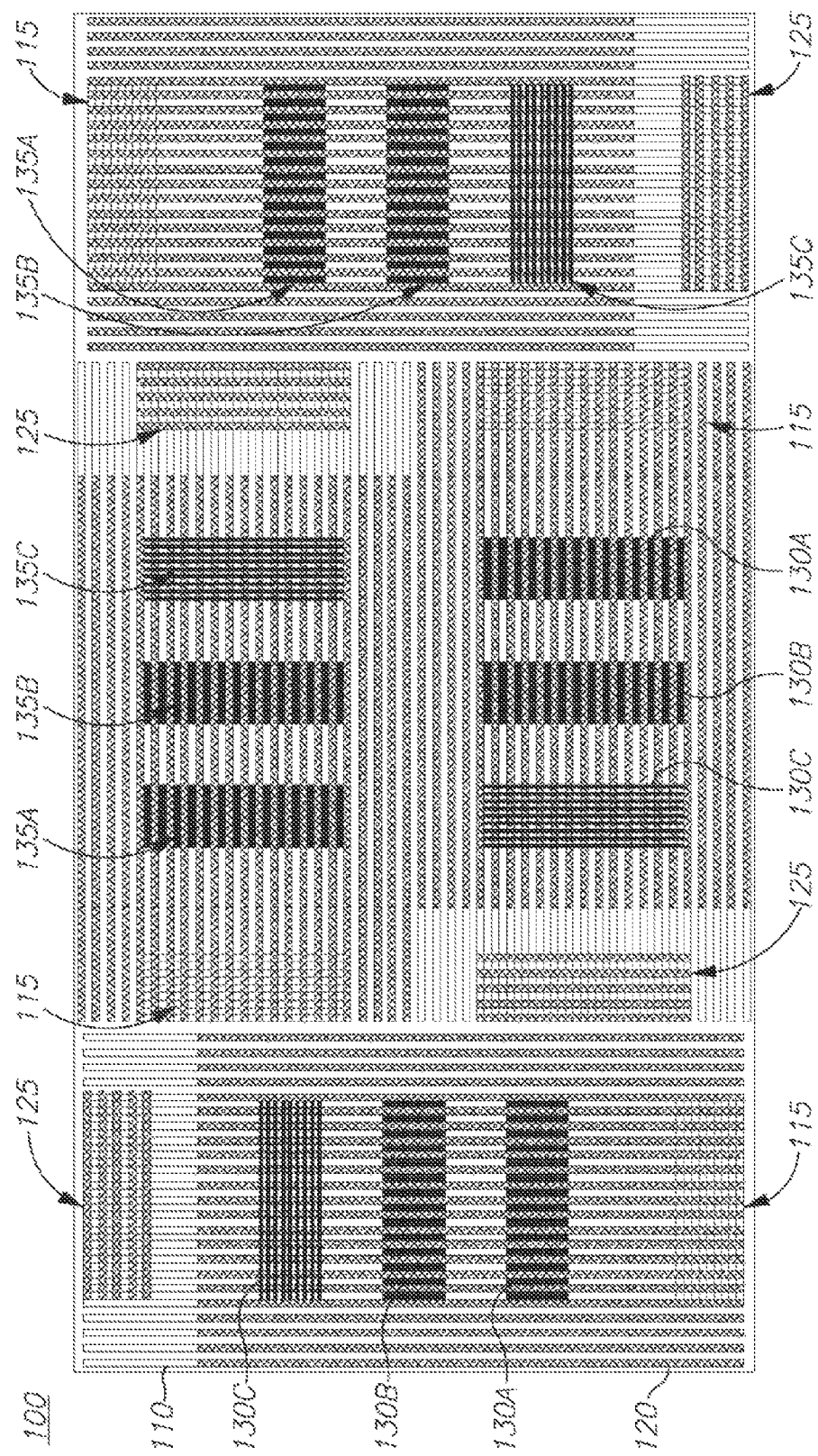
FIG. 3A is a high level schematic illustration of an exemplary multi-layered target, according to some embodiments of the invention.

FIGS. 3A and 3B are high level schematic illustrations of a multi-layered target 100 and its layers 110, 120, 130A, 130B, 130C, respectively, according to some embodiments of the invention. FIGS. 3A and 3B exemplify in a non-limiting manner process layer 110 (e.g., an oxide diffusion (OD) layer) having segmentation features 112A, 112B which may differ in different regions of layer 110; process layer 120 (e.g., a polysilicon (poly) layer) having segmentation features 122A, 122B which may differ in different regions of layer 120 but are parallel to segmentation features 112A, 112B (respectively) in specified overlapping regions in which segmentation features of layers 110 and 120 are parallel to each other; and multiple target layers 130A, 130B, 130C (e.g., contact layers) having respective target elements 135A, 135B, 135C in the specified regions in which segmentation features of layers 110 and 120 are parallel to each other. Layers 110, 120, 130A, 130B, 130C are shown separately in FIG. 3B and overlapping in FIG. 3A. It is noted that target elements 135A, 135B, 135C are perpendicular to parallel segmentation features of layer 110, 120 in each of the target regions.

It is noted that the illustrated identities and order of layers 110, 120 and 130A, 130B, 130C is non-limiting and any changes thereof are part of the present disclosure. Any of process layers 110, 120 may be below or above any of target layers 130A, 130B, 130C. Any of layers 110, 120, 130A, 130B and 130C may be applied as a positive or a negative layer. For example, any of target elements 135A, 135B, 135C may be gaps in full backgrounds of respective layers 130A, 130B, 130C. In another example, any of target elements 135A, 135B, 135C may be segmented, i.e., constructed of respective segments 134A, 134B, 134C which cumulatively form respective target elements 135A, 135B, 135C. Segmentation directions may vary among target elements 135A, 135B, 135C—both within each target layer 130A, 130B, 130C and between target layers 130A, 130B, 130C (e.g., segmentation direction in layer 130C is perpendicular to segmentation direction in layers 130A and 130B). Locally, in the specified regions, the orientation of any of target elements 135A, 135B, and 135C is perpendicular to the local parallel segmentation features of layers 110, 120. In case any of target elements 135A, 135B, 135C is a gap, respective segments 134A, 134B, 134C may be gaps. The pitches of any of the segmentation patterns may vary, particularly of segmentation patterns in different regions of each layer. For example, segmentation pitches in regions 112A and 112B may vary with respect to the direction of segmentation due to production considerations. While pitches may vary, pitches at the specified regions of any of target elements 135A, 135B, 135C are designed not to form Moiré patterns, e.g., be identical. In certain embodiments, the parallel segmentation features of the at least two process layers have the same segmentation pitch.

In certain embodiments, at least one of the process layers may comprise, outside the specified regions, target elements which are perpendicular to features of the other process layers. For example, process layer 120 comprises in FIGS. 3A and 3B target elements 125 which may be measured with respect to process layer 110; and process layer 110 comprises in FIGS. 3A and 3B target elements 115 which may be measured with respect to process layer 120. In case the background in any of layers 130A, 130B, 130C is segmented, its segmentation features in the regions of target elements 115 and/or 125 are parallel to segmentation features 122A, 122B and/or 112A, 112B in the respective regions and thus perpendicular to target elements 115, 125 respectively. According to such and similar embodiments, process layer 120 and/or 110 and any respective target layer 130A, 130B, 130C may have alternating roles, depending on the specified regions and targets 115, 125, 135A, 135B, 135C in each respective layer.

Figure 4B:
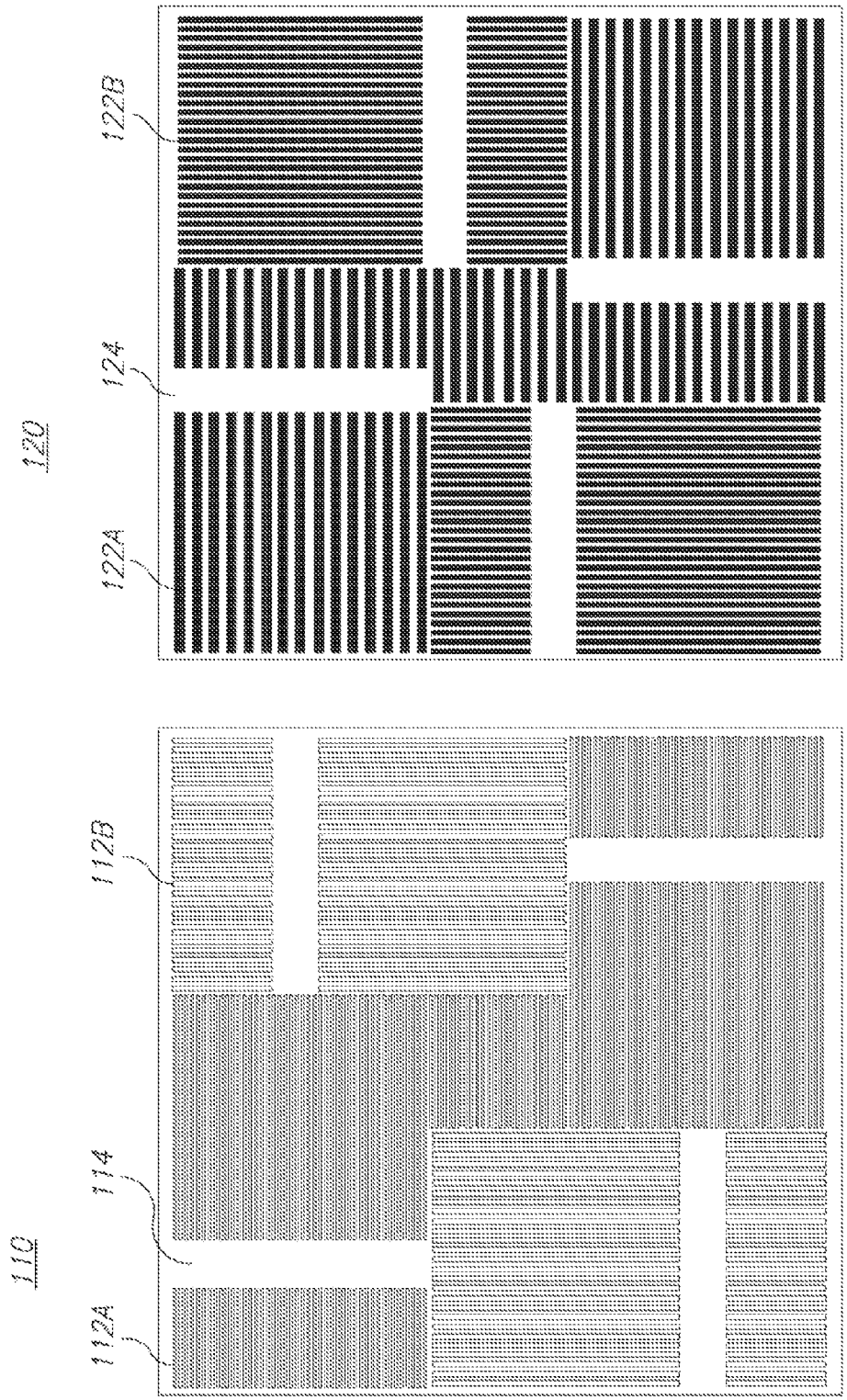
FIG. 4B is a high level schematic illustration of the layers of an exemplary multi-layered target, according to some embodiments of the invention; and, FIG. 5 is a high level flowchart illustrating a method, according to some embodiments of the invention.

FIGS. 4A and 4B are high level schematic illustrations of a multi-layered target 100 and its layers 110, 120, respectively, according to some embodiments of the invention. FIGS. 4A and 4B exemplify in a non-limiting manner process layer 110 (e.g., an oxide diffusion (OD) layer) having segmentation features 112A, 112B which may differ in orientation and segmentation parameters (e.g., pitch, feature width) in different regions of layer 110; and process layer 120 (e.g., a polysilicon (poly) layer) having segmentation features 122A, 122B which may differ in orientation and segmentation parameters (e.g., pitch, feature width) in different regions of layer 120 but are parallel to segmentation features 112A, 112B (respectively) in specified overlapping regions in which segmentation features of layers 110 and 120 are parallel to each other. Layers 110, 120 are shown separately in FIG. 4B and overlapping in FIG. 4A.

In certain embodiments, either or both layers 110, 120 may comprise features 114, 124 respectively which may be used as target elements 115, 125 with respect to the other layer 120, 110, respectively. It is noted that target elements 115, 125 are perpendicular to parallel segmentation features of layer 120, 110, respectively in each of the specified regions. Generally, at least one of the process layers may comprise, outside the specified regions, target elements which are perpendicular to features of the other process layers. For example, process layers 110, 120 comprise in FIGS. 4A and 4B gaps 114, 124 as target elements 115, 125 which may be measured with respect to process layers 120, 110 respectively.

It is noted that the illustrated identities and order of layers 110 and 120 is non-limiting and any changes thereof are part of the present disclosure. Process layers 110, 120 may be switched or multiple layers may be combined into multi-layered targets 100 according to the disclosed principles. Any of layers 110, 120 may be applied as a positive or a negative layer. Any of target elements 115, 125 may be gaps in a full or segmented background, be full elements or be segmented, i.e., constructed of segments as illustrated in FIG. 1B. The pitches of any of the segmentation patterns may vary, particularly of segmentation patterns in different regions of each layer. For example, segmentation pitches in regions 112A, 112B and 122A, 122B, respectively, may vary with respect to the direction of segmentation due to production considerations. While pitches may vary, pitches at the specified regions of target elements 115, 125 are designed not to form Moiré patterns, e.g., be identical to their background segmentation in the specified regions. In certain embodiments, the parallel segmentation features of the at least two process layers have the same segmentation pitch.

In any of the embodiments, parallel segmentation features at some of the specified regions may be configured to be perpendicular to the parallel segmentation features at other specified regions. Any of targets 100 may be configured to have a rotational symmetry of 180°, 120°, 90°, 60°, 45° and/or 30°.

FIG. 5 is a high level flowchart illustrating a method 200, according to some embodiments of the invention. Method 200 may comprise stages for designing and or producing targets 100, such as any of the following stages, irrespective of their order. Any of the designing and the configuring stages may be carried out by at least one computer processor. Certain embodiments comprise computer program products comprising a computer readable storage medium having computer readable program embodied therewith. The computer readable program may be configured to carry out stages of method 200. Also provided are design files which are produced according to stages of method 200. Certain embodiments comprise a computer program product comprising a computer readable storage medium having computer readable program embodied therewith. The computer readable program may be configured to carry out metrology measurements of targets 100 or any targets produced according to method 200.

Method 200 may comprise designing at least two process layers of a multi-layered target to have parallel segmentation features at specified regions (stage 210) and/or producing the process layers to have parallel segmentation features at specified regions (stage 215), and configuring target elements of at least one target layer of the multi-layered target to be perpendicular to the parallel segmentation features of the process layers at the specified regions (stage 220). Method 200 may further comprise producing the target elements to be perpendicular to the parallel segmentation features of the process layers at the specified regions (stage 225).

Method 200 may further comprise configuring the parallel segmentation features of the process layers to have the same pitch or at least not to form Moiré pattern(s) (stage 230) and/or designing the parallel segmentation features at some of the specified regions to be perpendicular to the parallel segmentation features at other specified regions (stage 240).

Method 200 may further comprise configuring target elements at process layer(s) outside the specified regions, which are perpendicular to the features of other process layers (stage 245) and/or designing distinct specified regions for target elements in different target layers (stage 280).

Method 200 may further comprise any of the following stages: configuring the target elements as full bars, gap bars and/or segmented bars (parallel or perpendicular to the parallel segmentation features) (stage 260); configuring a periphery of the target elements to be full, empty or segmented (stage 270); configuring the multi-layered target to have a rotational symmetry of any of 180°, 120°, 90°, 60°, 45° and 30° (stage 285).

Method 200 may further comprise carrying out the designing and/or the configuring by at least one computer processor (stage 290), as well as producing and/or providing target design files and/or metrology target. Method 200 may further comprise carrying out the respective metrology measurements of the disclosed targets as well.

Advantageously, disclosed multi-layered targets overcome several shortcomings of prior art targets, including for example process damage to the target itself and lack of compatibility of the target with semiconductor manufacturing design rules. Specific shortcomings include (i) violation of design rules for specific layers where orthogonal dummification (i.e., addition of dummyfill) is not allowed such as contacts to isolation which are not allowed on poly; (ii) dishing within or in the vicinity of the target due to chemical mechanical polishing; (iii) etch bias in the vicinity of the target due to incompatible pattern density; (iv) subsequent parasitic capacitance in the device due to design rule violation in the target; (v) lithographic incompatibility of the target causing metrology bias in the metrology result; and (vi) increase in metrology footprint on reticle and wafer due to excessive target size. Specifically, the present invention discloses improved methods for applying dummyfill to a target design and resulting targets.

Advantageously, disclosed multi-layered targets reveal and optimize specific dummyfill patterns and filling considerations which enable or enhance metrology measurements while conforming to design rules and thus producing accurate targets. As adding dummyfill to multi-layered target may quickly deteriorate the metrology measurement quality, the disclosed principles allow designing and producing viable metrology targets which nevertheless comprise dummyfill in form of the disclosed segmentation patterns.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A multi-layered target comprising:
   a first process layer including a first plurality of process layer segmentation features;

at least a second process layer including at least a second plurality of process layer segmentation features, wherein the at least a second process layer overlaps the first process layer at a plurality of target regions, wherein the first plurality of process segmentation features are substantially parallel to the at least a second plurality of process layer segmentation features within the plurality of target regions; and at least one target layer including a plurality of target elements, wherein each of the plurality of target elements are surrounded by an optically contrasting periphery element, wherein the at least one target layer overlaps the first process layer and the at least a second process layer at the plurality of target regions, wherein the plurality of target elements are substantially perpendicular to the first plurality of process layer segmentation features and the at least a second plurality of process layer segmentation features within the plurality of target regions, wherein the area of each of the plurality of target regions is defined by the area of a target element and surrounding periphery element.

2. The multi-layered target of claim 1, wherein the plurality of target elements includes at least one of:

a full bar, a gap bar, a bar segmented in parallel to the first plurality of process layer segmentation features and the at least a second plurality of process layer segmentation features, or a bar segmented perpendicularly to the first plurality of process layer segmentation features and the at least a second plurality of process layer segmentation features.

3. The multi-layered target of claim 1, wherein the plurality of target elements includes at least one of:

a bar segmented in parallel to the first plurality of process layer segmentation features and the at least a second plurality of process layer segmentation features within the plurality of target regions, wherein the at least one bar segmented in parallel is configured to create a Moiré pattern with the first plurality of process layer segmentation features and the at least a second plurality of process layer segmentation features within the plurality of target regions to facilitate ROI placement or target acquisition.

4. The multi-layered target of claim 1, wherein the periphery element includes at least one of:

a full pattern, an empty pattern, a segmented pattern substantially parallel to the first plurality of process layer segmentation features and the at least a second plurality of process layer segmentation features, or a segmented pattern substantially perpendicular to the first plurality of process layer segmentation features and the at least a second plurality of process layer segmentation features.

5. The multi-layered target of claim 1, wherein at least one of the first process layer or the at least a second process layer includes at least one target element outside the plurality of target regions, wherein the at least one target element in the first process layer is substantially perpendicular to the at least a second plurality of process layer segmentation features in the at least a second process layer, wherein the at least one target element in the at least a second process layer is substantially perpendicular to the first plurality of process layer segmentation features in the first process layer.

6. The multi-layered target of claim 1, wherein the first plurality of process layer segmentation features of the first process layer and the at least a second plurality of process layer segmentation features of the at least a second process layer have the same segmentation pitch.

7. The multi-layered target of claim 1, wherein the first plurality of process layer segmentation features of the first process layer has at least a first pitch, wherein the at least a second plurality of process layer segmentation features of the at least a second process layer has at least a second pitch, wherein the at least a first pitch and the at least a second pitch do not form a Moiré pattern.

8. The multi-layered target of claim 1, wherein the at least one target layer includes a plurality of target layers, wherein each of the plurality of target layers has a plurality of target elements in the plurality of target regions.

9. The multi-layered target of claim 1, wherein the plurality of target regions includes at least two target regions, wherein each of the at least two target regions includes a first plurality of process layer segmentation features, at least a second plurality of process layer segmentation features, and a plurality of target elements, wherein the at least two target regions are oriented based on a rotational symmetry of at least one of:

180 degrees, 120 degrees, 90 degrees, 60 degrees, or 30 degrees.

10. The multi-layered target of claim 1, wherein a first plurality of process layer segmentation features of a first process layer in a first target region of the plurality of target regions are perpendicular to at least a second plurality of process layer segmentation features of at least a second process layer in a second target region of the plurality of target regions.

11. A method comprising:

generating a first process layer of a multi-layer target including a first plurality of process layer segmentation features via at least one computer processor;

generating at least a second process layer of the multi-layer target including at least a second plurality of process layer segmentation features via the at least one computer processor, wherein the at least a second process layer overlaps the first process layer at a plurality of target regions, wherein the first plurality of process segmentation features are substantially parallel to the at least a second plurality of process layer segmentation features within the plurality of target regions; and generating at least one target layer including a plurality of target elements via the computer processor, wherein each of the plurality of target elements are surrounded by an optically contrasting periphery element, wherein the at least one target layer overlaps the first process layer and the at least a second process layer at the plurality of target regions, wherein the plurality of target elements are substantially perpendicular to the first plurality of process layer segmentation features and the at least a second plurality of process layer segmentation features within the plurality of target regions, wherein the area of each of the plurality of target regions is defined by the area of a target element and surrounding periphery element.

12. The method of claim 11, wherein the plurality of target elements includes at least one of:

a full bar, a gap bar, a bar segmented in parallel to the first plurality of process layer segmentation features and the at least a second plurality of process layer segmentation features, or a bar segmented perpendicularly to the first plurality of process layer segmentation features and the at least a second plurality of process layer segmentation features.

13. The method of claim 11, wherein the plurality of target elements includes at least one of:
a bar segmented in parallel to the first plurality of process layer segmentation features and the at least a second plurality of process layer segmentation features within the plurality of target regions, wherein the at least one bar segmented in parallel is configured to create a Moiré pattern with the first plurality of process layer segmentation features and the at least a second plurality of process layer segmentation features within the plurality of target regions to facilitate ROI placement or target acquisition.

14. The method of claim 11, wherein the periphery element includes at least one of:
a full pattern, an empty pattern, a segmented pattern substantially parallel to the first plurality of process layer segmentation features and the at least a second plurality of process layer segmentation features, or a segmented pattern substantially perpendicular to the first plurality of process layer segmentation features and the at least a second plurality of process layer segmentation features.

15. The method of claim 11, wherein at least one of the first process layer or the at least a second process layer includes at least one target element outside the plurality of target regions,
wherein the at least one target element in the first process layer is substantially perpendicular to the at least a second plurality of process layer segmentation features in the at least a second process layer,
wherein the at least one target element in the at least a second process layer is substantially perpendicular to the first plurality of process layer segmentation features in the first process layer.

16. The method of claim 11, wherein the first plurality of process layer segmentation features of the first process layer and the at least a second plurality of process layer segmentation features of the at least a second process layer have the same segmentation pitch.

17. The method of claim 11, wherein the first plurality of process layer segmentation features of the first process layer has at least a first pitch, wherein the at least a second plurality of process layer segmentation features of the at least a second process layer has at least a second pitch, wherein the at least a first pitch and the at least a second pitch do not form a Moiré pattern.

18. The method of claim 11, wherein the at least one target layer includes a plurality of target layers, wherein each of the plurality of target layers has a plurality of target elements in the plurality of target regions.

19. The method of claim 11, wherein the plurality of target regions includes at least two target regions, wherein each of the at least two target regions includes a first plurality of process layer segmentation features, at least a second plurality of process layer segmentation features, and a plurality of target elements, wherein the at least two target regions are oriented based on a rotational symmetry of at least one of:
180 degrees, 120 degrees, 90 degrees, 60 degrees, or 30 degrees.

20. The method of claim 11, wherein a first plurality of process layer segmentation features of a first process layer in a first target region of the plurality of target regions are perpendicular to at least a second plurality of process layer segmentation features of at least a second process layer in a second target region of the plurality of target regions.

21. The method of claim 11, further comprising:
generating a target design file for the multi-layered target via the at least one computer processor.

22. The method of claim 21, further comprising:
transmitting the target design file to a lithography tool, wherein the lithography tool is configured to produce a plurality of multi-layered targets based on a received target design file.

23. The method of claim 22, further comprising:
performing at least one metrology measurement on a plurality of multi-layered targets produced via the lithography tool.

24. A computer program product comprising:
a non-transitory computer readable storage medium having computer readable program embodied therewith, the computer readable program configured to cause at least one computer processor to:
generate a first process layer of a multi-layer target including a first plurality of process layer segmentation features via at least one computer processor;
generate at least a second process layer of the multi-layer target including at least a second plurality of process layer segmentation features via the at least one computer processor, wherein the at least a second process layer overlaps the first process layer at a plurality of target regions, wherein the first plurality of process segmentation features are substantially parallel to the at least a second plurality of process layer segmentation features within the plurality of target regions; and
generate at least one target layer including a plurality of target elements via the computer processor, wherein each of the plurality of target elements are surrounded by an optically contrasting periphery element, wherein the at least one target layer overlaps the first process layer and the at least a second process layer at the plurality of target regions, wherein the plurality of target elements are substantially perpendicular to the first plurality of process layer segmentation features and the at least a second plurality of process layer segmentation features within the plurality of target regions,
wherein the area of each of the plurality of target regions is defined by the area of a target element and surrounding periphery element.

25. A target design file for a lithography tool, wherein the target design file is configured to cause the lithography tool to produce:
a first process layer of a multi-layer target including a first plurality of process layer segmentation features via at least one computer processor;
at least a second process layer of the multi-layer target including at least a second plurality of process layer segmentation features via the at least one computer processor, wherein the at least a second process layer overlaps the first process layer at a plurality of target regions, wherein the first plurality of process segmentation features are substantially parallel to the at least a second plurality of process layer segmentation features within the plurality of target regions; and
at least one target layer including a plurality of target elements via the computer processor, wherein each of the plurality of target elements are surrounded by an optically contrasting periphery element, wherein the at least one target layer overlaps the first process layer and the at least a second process layer at the plurality of target regions, wherein the plurality of target elements are substantially perpendicular to the first plurality of process layer segmentation features and the at least a second plurality of process layer segmentation features within the plurality of target regions, wherein the area of each of the plurality of target regions is defined by the area of a target element and surrounding periphery element.

26. A method comprising:

producing a first process layer of a multi-layer target including a first plurality of process layer segmentation features via a lithography tool;

producing at least a second process layer of the multi-layer target including at least a second plurality of process layer segmentation features via the lithography tool, wherein the at least a second process layer overlaps the first process layer at a plurality of target regions, wherein the first plurality of process segmentation features are substantially parallel to the at least a second plurality of process layer segmentation features within the plurality of target regions; and producing at least one target layer including a plurality of target elements via the lithography tool, wherein each of the plurality of target elements are surrounded by an optically contrasting periphery element, wherein the at least one target layer overlaps the first process layer and the at least a second process layer at the plurality of target regions, wherein the plurality of target elements are substantially perpendicular to the first plurality of process layer segmentation features and the at least a second plurality of process layer segmentation features within the plurality of target regions, wherein the area of each of the plurality of target regions is defined by the area of a target element and surrounding periphery element.

27. The method of claim 26, wherein the plurality of target elements includes at least one of:

a full bar, a gap bar, a bar segmented in parallel to the first plurality of process layer segmentation features and the at least a second plurality of process layer segmentation features, or a bar segmented perpendicularly to the first plurality of process layer segmentation features and the at least a second plurality of process layer segmentation features.

28. The method of claim 26, wherein the plurality of target elements includes at least one of:

a bar segmented in parallel to the first plurality of process layer segmentation features and the at least a second plurality of process layer segmentation features within the plurality of target regions, wherein the at least one bar segmented in parallel is configured to create a Moiré pattern with the first plurality of process layer segmentation features and the at least a second plurality of process layer segmentation features within the plurality of target regions to facilitate ROI placement or target acquisition.

29. The method of claim 26, wherein the periphery element includes at least one of:

a full pattern, an empty pattern, a segmented pattern substantially parallel to the first plurality of process layer segmentation features and the at least a second plurality of process layer segmentation features, or a segmented pattern substantially perpendicular to the first plurality of process layer segmentation features and the at least a second plurality of process layer segmentation features.

30. The method of claim 26, wherein at least one of the first process layer or the at least a second process layer includes at least one target element outside the plurality of target regions, wherein the at least one target element in the first process layer is substantially perpendicular to the at least a second plurality of process layer segmentation features in the at least a second process layer, wherein the at least one target element in the at least a second process layer is substantially perpendicular to the first plurality of process layer segmentation features in the first process layer.

31. The method of claim 26, wherein the first plurality of process layer segmentation features of the first process layer and the at least a second plurality of process layer segmentation features of the at least a second process layer have the same segmentation pitch.

32. The method of claim 26, wherein the first plurality of process layer segmentation features of the first process layer has at least a first pitch, wherein the at least a second plurality of process layer segmentation features of the at least a second process layer has at least a second pitch, wherein the at least a first pitch and the at least a second pitch do not form a Moiré pattern.

33. The method of claim 26, wherein the at least one target layer includes a plurality of target layers, wherein each of the plurality of target layers has a plurality of target elements in the plurality of target regions.

34. The method of claim 26, wherein the plurality of target regions includes at least two target regions, wherein each of the at least two target regions includes a first plurality of process layer segmentation features, at least a second plurality of process layer segmentation features, and a plurality of target elements, wherein the at least two target regions are oriented based on a rotational symmetry of at least one of:

180 degrees, 120 degrees, 90 degrees, 60 degrees, or 30 degrees.

35. The method of claim 26, wherein a first plurality of process layer segmentation features of a first process layer in a first target region of the plurality of target regions are perpendicular to at least a second plurality of process layer segmentation features of at least a second process layer in a second target region of the plurality of target regions.

36. The method of claim 26, further comprising:

receiving a target design file for the multi-layered target, the target design file generated by at least one computer processor.

37. The method of claim 36, further comprising:

producing a plurality of multi-layered targets from the received target design file via the lithography tool.

38. The method of claim 37, further comprising:

performing at least one metrology measurement on the plurality of multi-layered targets produced via the lithography tool.

39. A computer program product comprising:

a non-transitory computer readable storage medium having computer readable program embodied therewith, the computer readable program configured to cause one or more computer processors to:

direct a lithography tool to produce a first process layer of a multi-layer target including a first plurality of process layer segmentation features;

direct the lithography tool to produce at least a second process layer of the multi-layer target including at least a second plurality of process layer segmentation features, wherein the at least a second process layer overlaps the first process layer at a plurality of target regions, wherein the first plurality of process segmentation features are substantially parallel to the at least a second plurality of process layer segmentation features within the plurality of target regions; and direct the lithography tool to produce at least one target layer including a plurality of target elements, wherein each of the plurality of target elements are surrounded by an optically contrasting periphery element, wherein the at least one target layer overlaps the first process layer and the at least a second process layer at the plurality of target regions, wherein the plurality of target elements are substantially perpendicular to the first plurality of process layer segmentation features and the at least a second plurality of process layer segmentation features within the plurality of target regions, wherein the area of each of the plurality of target regions is defined by the area of a target element and surrounding periphery element.

\* \* \* \* \*